(12) United States Patent
Troili

(10) Patent No.: US 11,712,528 B2
(45) Date of Patent: Aug. 1, 2023

(54) BREATHING APPARATUS, METHOD OF CONTROLLING A BREATHING APPARATUS, COMPUTER PROGRAM AND COMPUTER PROGRAM PRODUCT

(71) Applicant: Maquet Critical Care AB, Solna (SE)

(72) Inventor: Carl-Erik Troili, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 566 days.

(21) Appl. No.: 16/620,646

(22) PCT Filed: Jul. 5, 2017

(86) PCT No.: PCT/SE2017/050750
§ 371 (c)(1),
(2) Date: Dec. 9, 2019

(87) PCT Pub. No.: WO2019/009771
PCT Pub. Date: Oct. 1, 2019

(65) Prior Publication Data
US 2020/0188615 A1 Jun. 18, 2020

(51) Int. Cl.
*A61M 16/00* (2006.01)
*A61M 16/20* (2006.01)
*A61M 16/08* (2006.01)

(52) U.S. Cl.
CPC ...... *A61M 16/0069* (2014.02); *A61M 16/202* (2014.02); *A61M 16/024* (2017.08);
(Continued)

(58) Field of Classification Search
CPC ............ A61M 16/0069; A61M 16/202; A61M 16/024; A61M 16/0833; A61M 2202/0208; A61M 16/1005
See application file for complete search history.

(56) References Cited

U.S. PATENT DOCUMENTS 5,735,268 A * 4/1998 Chua ................... A61M 16/024
128/207.14
6,520,180 B1 2/2003 Sahmlow et al.
(Continued)

FOREIGN PATENT DOCUMENTS

CA 2201698 10/1998
DE 10014959 5/2001
(Continued)

*Primary Examiner* — Margaret M Luarca
(74) *Attorney, Agent, or Firm* — Fay Kaplun & Marcin, LLP

(57) ABSTRACT

A breathing apparatus (1) is disclosed comprising an inspiratory channel (3), an expiratory channel (4), a patient interface (5), an oxygen valve (13) and a blower (7) comprising blower driving means (9). The blower (7) is arranged to produce a flow of air to the inspiratory channel (3). The oxygen valve (13) is configured to selectively deliver a flow of oxygen to the inspiratory channel (3). The breathing apparatus further comprises a control unit (19) configured to control the blower driving means (9) so that the blower (7) produces substantially no flow of air to the inspiratory channel (3) during a time period (tp). The present disclosure further relates to a method (100) of controlling operation of a breathing apparatus (1), a computer program and a computer program product (300) for performing a method (100) of controlling operation of a breathing apparatus (1).

31 Claims, 6 Drawing Sheets

(52) U.S. Cl.
CPC ....... *A61M 16/0833* (2014.02); *A61M 16/208* (2013.01); *A61M 2016/0027* (2013.01); *A61M 2016/0033* (2013.01); *A61M 2202/0208* (2013.01); *A61M 2205/8206* (2013.01); *A61M 2230/40* (2013.01)

(56) References Cited

U.S. PATENT DOCUMENTS

| | | |
|---|---|---|
| 2016/0151597 A1 | 6/2016 | Baecke et al. |
| 2016/0287824 A1 | 10/2016 | Chang |
| 2019/0160246 A1* | 5/2019 | Saitou .................. A61M 16/06 |

FOREIGN PATENT DOCUMENTS

| | | |
|---|---|---|
| WO | 2000/45883 | 8/2000 |
| WO | 2002/28460 | 4/2002 |
| WO | 2004/112680 | 12/2004 |

* cited by examiner

BREATHING APPARATUS, METHOD OF CONTROLLING A BREATHING APPARATUS, COMPUTER PROGRAM AND COMPUTER PROGRAM PRODUCT

TECHNICAL FIELD

The present invention relates to a breathing apparatus, in particular to a breathing apparatus comprising a blower. The present invention further relates to a method of controlling operation of a breathing apparatus, a computer program for performing a method of controlling operation of a breathing apparatus and a computer program product for performing a method of controlling operation of a breathing apparatus.

BACKGROUND

Breathing apparatuses are used to assist patients having difficulty either oxygenating the blood or getting rid of carbon dioxide in the blood or both by assisting their breathing. In order to ensure that sufficient oxygen is available in the lungs, a breathing apparatus may be used to mechanically assist or replace spontaneous breathing. A breathing apparatus works by increasing the patient's airway pressure through a patient interface, such as a mask or an endotracheal tube or tracheostomy tube. The increased pressure forces air to flow into the lungs. When the breathing apparatus reduces the pressure, the elastic contraction of the chest collapses the lungs and pushes a volume of air out. The volume of air that is introduced into, and pushed out of, the lungs during each breathing cycle is usually referred to as "tidal volume".

Some breathing apparatuses comprise a blower and an oxygen valve, wherein the oxygen valve is connected to a pressurized oxygen source. In such breathing apparatuses, the blower may be arranged to produce a flow of air to an inspiratory channel and the oxygen valve may be configured to selectively deliver a flow of oxygen from a pressurized oxygen source to the inspiratory channel.

There are several separate problems associated with such breathing apparatuses that may be addressed. Generally, a blower is inefficient in maintaining a pressure and is relatively slow in achieving an increase in pressure, as well as in achieving a decrease in pressure. Further, a blower requires a lot of energy to produce a flow of air to the patient interface, which may affect the runtime of a breathing apparatus that is powered by batteries. In addition, the blower is a vital component of the breathing apparatus and is subjected to wear during use. Another problem is that normally, an unwanted increase in flow is obtained in the inspiratory channel during an onset of an expiration phase. The flow of air in the inspiratory channel, obtained during an inspiration phase, continues into a portion of an expiration phase. This occurs because the inertia of the blower makes it deliver a high flow if the pressure is reduced faster than the rotation of the blower is reduced. This flow through both the inspiratory limb and the expiratory limb will increase the expiratory WOB as well as increase the oxygen consumption if a specific oxygen concentration shall be kept. Thus, a patient is, as a result thereof, subjected to a flow of air in the inspiratory channel, when the patient is about to exhale. Such a flow of air may be uncomfortable for the patient.

Another problem that may be addressed is oxygen consumption. In breathing apparatuses comprising a source of oxygen, this source of oxygen may be a high pressure oxygen bottle, an oxygen concentrator or a thermos with liquefied oxygen all of which may limiting the usage of the ventilator. In breathing apparatuses comprising an oxygen concentrator, the concentration of oxygen from ambient air requires considerable amount of energy. Accordingly, it is an advantage if oxygen from the oxygen source is used sparingly.

Another problem that may be addressed is performance of the breathing apparatus. The performance of the breathing apparatus may be subdivided into several operational aspects of the breathing apparatus. An example of such an operational aspect is rise and fall times which is the ability of the breathing apparatus to perform rapid changes of pressure and/or flow. Another example is Work Of Breathing (WOB), which is a measure of the resistance a patient is facing when breathing. The resistance during inspiration is usually referred to as inspiratory work of breathing, and the resistance during expiration is usually referred to as expiratory work of breathing. A further example is Trigger Delay which is a cause of inspiratory work of breathing. Trigger Delay is the delay between the beginning of an inspiration phase and the detection of the beginning of the inspiration phase. A still further example is the pressure dip during inspiratory trigger detection, which is the maximum pressure dip below positive end-expiratory pressure (PEEP) before the pressure starts to recover. Still further examples are Pressure Time product 300 ms (PTP300), Pressure Time product 500 ms (PTP500), etc, which are measures of quality describing how much the breathing apparatus deviates from an ideal curve shape. The different Pressure Time products 300 ms, 500 ms, etc., is a combination of the pressure delay measurement and the rise time of the pressure curve.

SUMMARY

It is an object of this disclosure to overcome, or at least alleviate, at least some of the above-mentioned problems and drawbacks.

According to an aspect of this disclosure, the above object is achieved by a breathing apparatus comprising an inspiratory channel, an expiratory channel and a patient interface. The inspiratory channel and the expiratory channel are connected to the patient interface. The breathing apparatus further comprises a blower comprising blower driving means. The blower is arranged to produce a flow of air to the inspiratory channel. The breathing apparatus further comprises an oxygen valve arranged to be connected to a oxygen source. The oxygen valve is configured to selectively deliver a flow of oxygen from the oxygen source to the inspiratory channel. The breathing apparatus further comprises a valve configured to prevent flow of gas in a direction from the patient interface in the inspiratory channel. Furthermore, the breathing apparatus further comprises a detecting unit configured to detect breathing phases, and a control unit connected to the blower driving means, the oxygen valve and the detecting unit. The control unit is configured to control the blower driving means so that the blower produces substantially no flow of air to the inspiratory channel during a time period starting after 30% of a duration of an inspiration phase and ending the latest upon initiation of the subsequent inspiration phase.

In other words, the control unit is configured to control the blower driving means so that substantially no flow of air to the inspiratory channel is provided by the blower to the inspiratory channel during the transition between expiratory phase and inspiratory phase of the breath cycle. See FIG. 4 for a measure of what constitutes substantially no flow of air produced by the blower to the inspiratory channel during this portion of a breath cycle, i.e. during the time period of the breath cycle.

Since the control unit is configured to control the blower driving means so that the blower produces substantially no flow of air to the inspiratory channel during a time period starting after 30% of a duration of an inspiration phase and ending the latest upon initiation of the subsequent inspiration phase, the energy consumption of the breathing apparatus is reduced. Furthermore, the life length of the blower is increased due to less wear and tear. Since the time period starts after 30% of a duration of an inspiration phase and ends the latest upon initiation of the subsequent inspiration phase, a patient breathing through the patient interface will not experience a noticeable degradation of work of breathing. Thus, the control of the blower driving means so that the blower produces substantially no flow of air to the inspiratory channel during the time period will not significantly affect the performance of the breathing apparatus in a negative manner.

Accordingly, as shown above, a breathing apparatus is provided overcoming, or at least alleviating, at least some of the above-mentioned problems and drawbacks. As a result, the above-mentioned object is achieved.

Optionally, the control unit is configured to deactivate the blower driving means during the time period. Thereby, the energy consumption of the breathing apparatus is further reduced and the life length of the blower is further increased.

Optionally, the time period starts during the inspiration phase and ends during the subsequent expiration phase. Thereby, the time period will last over a transition area between the inspiration phase and the expiration phase. Accordingly, the blower will produce substantially no flow of air to the inspiratory channel in the transition area between the inspiration phase and the expiration phase. As a result, the increase in flow normally obtained in the inspiratory channel during an onset of the expiration phase is eliminated, or at least significantly reduced. Thereby, the flow of gas which normally is flowing towards the patient in the inspiratory channel, when the patient is about to exhale, is eliminated, or at least significantly reduced. As a result, the work of breathing is improved for the patient. In addition, consumption of oxygen can be reduced by eliminating, or reducing, the increase in flow normally obtained in the inspiratory channel during an onset of the expiration phase. Thus, a breathing apparatus is provided with improved performance while being capable of reducing consumption of oxygen at the same time.

Optionally, the time period starts during a final portion of the inspiration phase and ends during an onset of the subsequent expiration phase. Thereby, energy consumption of the breathing apparatus is reduced, the increase in flow normally obtained in the inspiratory channel during an onset of the expiration phase is eliminated, or at least significantly reduced, thus improving the work of breathing and providing conditions for a reduced consumption of oxygen.

Optionally, the time period starts during a final portion of the inspiration phase and ends during 50%-75% of a duration of the subsequent expiration phase. Thereby, the energy consumption of the breathing apparatus is further reduced and the life length of the blower is further increased and the increase in flow normally obtained in the inspiratory channel during an onset of the expiration phase is eliminated, or at least significantly reduced, thus improving the work of breathing and providing conditions for a reduced consumption of oxygen.

Optionally, the control unit is configured to control the oxygen valve to increase delivered flow of oxygen from the oxygen source to the inspiratory channel during at least a portion of the time period. Thereby, the absence of flow from the blower is compensated for during at least a portion of the time period. By compensating the absence of flow from the blower with a flow of oxygen from the oxygen source, the rise and fall times can be significantly improved since the oxygen valve is much quicker in increasing and decreasing flow and pressure than the blower. Also, the pressure time product can be improved since the oxygen valve is much quicker in increasing and decreasing flow and pressure than the blower, and because the oxygen valve is capable of providing a more precise control of flow and pressure than the blower. Accordingly, a breathing apparatus is provided capable of improving performance, while the energy consumption is reduced and the life length of the blower is increased.

Optionally, the control unit is configured to control the oxygen valve to increase delivered flow of oxygen from the oxygen source to the inspiratory channel during an initial portion of the time period. Thereby, the absence of flow from the blower during the initial portion of the time period is compensated for by the oxygen valve. The performance of the breathing apparatus can be further improved by compensating the absence of flow from the blower with a flow of oxygen from the oxygen source during the initial portion of the time period. In this way the rise and fall times, and the pressure time product, can be improved because the oxygen valve is much quicker in increasing and decreasing flow and pressure than the blower, and since the oxygen valve is capable of providing a more precise control of flow and pressure than the blower.

Optionally, the control unit is configured to control the oxygen valve to increase delivered flow of oxygen from the oxygen source to the inspiratory channel during an initial portion of the inspiration phase. Thereby, the rise time of the pressure and flow obtained in the inspiratory channel upon the initial portion of the inspiration phase is reduced. This occurs because the oxygen valve is faster than the blower in increasing the pressure and flow. In addition, consumption of oxygen can be reduced, since in principle, when a patient inhales and exhales, only the first 75% of the breath is used for transporting oxygen to the patient and carbon dioxide from the patient. By increasing the amount of oxygen delivered to the patient during an initial portion of the inspiration phase, the oxygen consumption by the breathing apparatus can be significantly reduced because less oxygen is wasted. During high leakage situations, the effect is even stronger. Accordingly, a breathing apparatus is provided with improved performance, which is capable of reducing consumption of oxygen during its operation.

Optionally, the control unit is configured to control the oxygen valve to deliver a flow of oxygen from the oxygen source to the inspiratory channel from an onset of the inspiration phase to 40%-100% of the duration of the inspiration phase. Thereby, the absence of flow from the blower is compensated for during a great proportion of the inspiration phase by the oxygen source. Furthermore, according to these embodiments, the breathing apparatus can be used to perform a lung recruitment manoeuvre, even in cases where the blower is producing a low flow of air to the inspiratory channel, or substantially no flow of air to the inspiratory channel, as will be further explained below. According to some embodiments, the control unit is configured to control the oxygen valve to deliver a flow of oxygen from the oxygen source to the inspiratory channel from an onset of the inspiration phase to 100% of the duration of the inspiration phase, i.e. to the end of the inspiration phase.

Optionally, the control unit is configured to control the oxygen valve to increase delivered flow of oxygen from the oxygen source to the inspiratory channel during a final portion of the inspiration phase. Thereby, the absence of flow from the blower is compensated for during the final portion of the inspiration phase by the oxygen source. By compensating the absence of flow from the blower with a flow of oxygen from the oxygen source during the final portion of the inspiration phase, the performance of the breathing apparatus can be improved. This occurs because the rise and fall times can be improved because the oxygen valve is much quicker in increasing and decreasing flow and pressure than the blower, and since the oxygen valve is capable of providing a more precise control of flow and pressure than the blower. Furthermore, the increase in flow normally obtained in the inspiratory channel during an onset of the expiration phase is eliminated, or at least significantly reduced, thus improving the work of breathing and providing conditions for a reduced consumption of oxygen. Accordingly, a breathing apparatus is provided with reduced energy consumption and increased life length of the blower, while the performance of the breathing apparatus can be further improved.

Optionally, the control unit is configured to control the oxygen valve to deliver a flow of oxygen from the oxygen source to the inspiratory channel during a second time period lasting from an onset of the inspiration phase to 10%-30% of the duration of the inspiration phase. Thereby, the consumption of oxygen can be significantly reduced. This occurs in principle because when a patient inhales and exhales, only the first 75% of the breath is used for transporting oxygen to the patient and carbon dioxide from the patient. By only delivering oxygen to the patient during the first phase of the inspiration phase, the oxygen consumption by the breathing apparatus is significantly reduced because less oxygen is wasted. During high leakage situations, the effect will be even stronger. Furthermore, rise time of the pressure in the inspiratory channel, during the initial portion of the inspiration phase, is reduced because the oxygen valve is faster than the blower in increasing the pressure and flow in the inspiratory channel, thus improving the work of breathing. In addition, the pressure time product can be improved because the oxygen valve is much quicker in increasing and decreasing flow and pressure than the blower, and since the oxygen valve is capable of providing a more precise control of flow and pressure than the blower.

Optionally, the control unit is configured to control the oxygen valve to deliver a flow of oxygen from the oxygen source to the inspiratory channel during the expiration phase. Thereby, the absence of flow produced by the blower can be compensated for during the expiration phase by the oxygen source. In addition, the inspiratory channel will be filled with oxygen during the expiration phase. Thereby, an amount of oxygen will be present in the inspiratory channel upon the initiation of the subsequent inspiration phase, which potentially further can reduce consumption of oxygen by the breathing apparatus by reducing oxygen waste. Still further, the delivery of a flow of oxygen from the oxygen source to the inspiratory channel during the expiration phase provides a bias flow, in the absence of a flow produced by the blower, and this bias flow can be used to facilitate detection of a transition between the expiration phase and the inspiration phase. In this way, the Trigger Delay can be reduced.

Optionally, the control unit is configured to control the blower to deliver a flow of air to the inspiratory channel during the expiration phase. In this way, the inspiratory channel will be filled with air during the expiration phase. As a result, a lung recruitment manoeuvre can be performed in the subsequent inspiration phase, using the oxygen valve, without subjecting the patient to an unnecessarily high concentration of oxygen. A too high concentration of oxygen may inflict alveolar collapse if the patient is exposed for longer time periods for example.

Optionally, the breathing apparatus further comprises an input unit connected to the control unit, wherein the input unit is configured to provide selection of a mode of operation among at least two different modes of operation, and wherein the control unit is configured to adapt the time period on the basis of the selected mode of operation. In this manner, a breathing apparatus is provided capable of adapting operation in dependence of at least two different modes of operation.

Optionally, the control unit is configured to control the oxygen valve on the basis of the selected mode of operation, and wherein the at least two different modes of operation comprises at least two modes of operation in which different operational aspects of the breathing apparatus are optimized. In this manner, a breathing apparatus is provided capable of optimizing at least two different operational aspects of the breathing apparatus by controlling the blower and the oxygen valve.

Optionally, the breathing apparatus comprises one or more batteries connected to the blower driving means to supply driving energy to the blower driving means. Thereby, a breathing apparatus is provided capable of operating without any external power source being available. Furthermore, because the breathing apparatus provided is capable of operating in an energy efficient manner, life length of the one or more batteries can be prolonged.

According to a second aspect of this disclosure, the object is achieved by a method of controlling a breathing apparatus, wherein the breathing apparatus comprises:
  an inspiratory channel, an expiratory channel and a patient interface, wherein the inspiratory channel and the expiratory channel are connected to the patient interface,
  a blower comprising blower driving means, wherein the blower is arranged to produce a flow of air to the inspiratory channel,
  an oxygen valve connected to a oxygen source, wherein the oxygen valve is configured to selectively deliver a flow of oxygen from the oxygen source to the inspiratory channel,
  a valve configured to prevent flow of gas in a direction from the patient interface in the inspiratory channel,
  a detecting unit configured to detect breathing phases, and
  a control unit connected to the blower driving means, the oxygen valve and the detecting unit, wherein the method comprises the steps of:
    detecting breathing phases, using the detecting unit, and
    controlling the blower driving means, using the control unit, so that the blower produces substantially no flow of air to the inspiratory channel during a time period starting after 30% of a duration of an inspiration phase and ending the latest upon initiation of the subsequent inspiration phase.

Since the method comprises controlling the blower driving means so that the blower produces essentially or substantially no flow of air to the inspiratory channel during a time period starting after 30% of a duration of an inspiration phase and ending the latest upon initiation of the subsequent inspiration phase, the energy consumption of the breathing apparatus is reduced. Furthermore, the life length of the blower is increased due to less wear and tear. Since the time period starts after 30% of a duration of an inspiration phase and ends the latest upon initiation of the subsequent inspiration phase, a patient breathing through the patient interface will not experience a noticeable degradation of work of breathing. Thus, the controlling of the blower driving means so that the blower produces substantially no flow of air to the inspiratory channel will not significantly affect the performance of the breathing apparatus in a negative manner.

Accordingly, as described above, a method is provided overcoming, or at least alleviating, at least some of the above-mentioned problems and drawbacks. As a result, the above-mentioned object is achieved.

Optionally, the method comprises the step of:
deactivating the blower driving means during the time period, using the control unit.

In this way, the energy consumption of the breathing apparatus is further reduced and the life length of the blower is further increased.

Optionally, the method comprises the steps of:
starting the time period during the inspiration phase, and
ending the time period during the subsequent expiration phase.

In this way, the time period will last over a transition area between the inspiration phase and the expiration phase. Accordingly, no flow of air will be produced to the inspiratory channel in the transition area between the inspiration phase and the expiration phase. As a result, the increase in flow normally obtained in the inspiratory channel during an onset of the expiration phase is eliminated, or at least significantly or substantially reduced. As a result, the flow of gas that normally is flowing towards the patient in the inspiratory channel, when the patient is about to exhale, is eliminated, or at least significantly reduced. In this way, the work of breathing is improved. In addition, consumption of oxygen can be reduced by eliminating, or reducing, the increase in flow normally obtained in the inspiratory channel during an onset of the expiration phase. Thus, a method is provided capable of improving performance of a breathing apparatus and reducing consumption of oxygen by the breathing apparatus.

Optionally, the method comprises the steps of:
starting the time period during a final portion of the inspiration phase, and
ending the time period during an onset of the subsequent expiration phase.

Thereby, a method is provided reducing the energy consumption of the breathing apparatus. In addition, the increase in flow normally obtained in the inspiratory channel during an onset of the expiration phase is eliminated, or at least significantly reduced, thus improving the work of breathing.

Optionally, the method comprises the steps of:
starting the time period during a final portion of the inspiration phase, and
ending the time period during 50%-75% of a duration of the subsequent expiration phase.

In this way, a method is provided capable of further reducing the energy consumption of the breathing apparatus and further increasing the life length of the blower. In addition, the increase in flow normally obtained in the inspiratory channel during an onset of the expiration phase is eliminated, or at least significantly reduced, thus improving the work of breathing. According to some embodiments, the final portion of the inspiration phase is between 65% and 95% of the duration of the inspiration phase.

Optionally, the method comprises the step of:
controlling the oxygen valve to increase delivered flow of oxygen from the oxygen source to the inspiratory channel during at least a portion of the time period, using the control unit.

In this way, the absence of flow from the blower is compensated for during at least a portion of the time period. By compensating the absence of flow from the blower with a flow of oxygen from the oxygen source, the rise and fall times can be significantly improved since the oxygen valve is much quicker in increasing and decreasing flow and pressure than the blower. Also, the pressure time product can be improved since the oxygen valve is much quicker in increasing and decreasing flow and pressure than the blower, and because the oxygen valve is capable of providing a more precise control of flow and pressure than the blower. Accordingly, a method is provided capable of improving performance of a breathing apparatus, while the energy consumption is reduced and the life length of the blower is increased.

Optionally, the method comprises the step of:
controlling the oxygen valve to increase delivered flow of oxygen from the oxygen source to the inspiratory channel during an initial portion of the time period, using the control unit.

In this way, the absence of flow from the blower during the initial portion of the time period is compensated for by oxygen flow from the oxygen source. The performance of the breathing apparatus can thus be further improved by compensating the absence of flow from the blower with a flow of oxygen from the oxygen source during the initial portion of the time period. This occurs because the rise and fall times, and the pressure time product, can be improved since the oxygen valve is much quicker in increasing and decreasing flow and pressure than the blower, and because the oxygen valve is capable of providing a more precise control of flow and pressure than the blower.

Optionally, the method comprises the step of:
controlling the oxygen valve to increase delivered flow of oxygen from the oxygen source to the inspiratory channel during an initial portion of the inspiration phase, using the control unit.

In this way, the rise time is reduced of the pressure and flow obtained in the inspiratory channel upon the initial portion of the inspiration phase. This occurs because the oxygen valve is faster than the blower in increasing the pressure and flow. In addition, consumption of oxygen can be reduced because, in principle, when a patient inhales and exhales, only the first 75% of the breath is used for transporting oxygen to the patient and carbon dioxide from the patient. By increasing the amount of oxygen delivered to the patient during an initial portion of the inspiration phase, the oxygen consumption can be significantly reduced because less oxygen is wasted by the breathing apparatus. During high leakage situations, the effect is even stronger. Accordingly, a method is provided capable of improving performance of a breathing apparatus and reducing consumption of oxygen thereof by delivering oxygen in a more efficient way.

Optionally, the method comprises the step of:
controlling the oxygen valve to deliver a flow of oxygen from the oxygen source to the inspiratory channel from an onset of the inspiration phase to 40%-100% of the duration of the inspiration phase, using the control unit.

In this way, the absence of flow from the blower is compensated for during a great proportion of the inspiration phase by oxygen flow from the oxygen source. Furthermore, according to these embodiments, the method can be used to perform a lung recruitment manoeuvre, even in cases where the blower is producing a low flow of air to the inspiratory channel, or substantially no flow of air to the inspiratory channel, as will be further explained below. According to some embodiments, the method comprises controlling the oxygen valve to deliver a flow of oxygen from the oxygen source to the inspiratory channel from an onset of the inspiration phase to 100% of the duration of the inspiration phase, i.e. to the end of the inspiration phase.

Optionally, the method comprises the step of:
controlling the oxygen valve to increase delivered flow of oxygen from the oxygen source to the inspiratory channel during a final portion of the inspiration phase, using the control unit.

In this way, the absence of flow from the blower is compensated for during the final portion of the inspiration phase by oxygen flow from the oxygen source. By compensating the absence of flow from the blower with a flow of oxygen from the oxygen source during the final portion of the inspiration phase, the performance of the breathing apparatus can be improved. This occurs because the rise and fall times, and the pressure time product, can be improved because the oxygen valve is much quicker in increasing and decreasing flow and pressure than the blower, and because the oxygen valve is capable of providing a more precise control of flow and pressure than the blower. Accordingly, a method is provided capable of reducing energy consumption of a breathing apparatus, increasing life length of the blower, while improving the performance of the breathing apparatus.

Optionally, the method comprises the step of:
controlling the oxygen valve to deliver a flow of oxygen from the oxygen source to the inspiratory channel during a second time period lasting from an onset of the inspiration phase to 10%-30% of the duration of the inspiration phase, using the control unit.

In this way, the consumption of oxygen by the breathing apparatus can be significantly reduced. This occurs because, in principle, when a patient inhales and exhales during a breathing cycle, only the first 75% of the breath is used for transporting oxygen to the patient and carbon dioxide from the patient. By only delivering oxygen to the patient during the first phase of the inspiration phase, the oxygen consumption by the breathing apparatus is significantly reduced. During high leakage situations, the effect will be even stronger. Furthermore, rise time of the pressure obtained in the inspiratory channel, during the initial portion of the inspiration phase, is reduced because the oxygen valve is faster than the blower in increasing the pressure and flow in the inspiratory channel, thus improving the work of breathing. In addition, the pressure time product can be improved because the oxygen valve is much quicker in increasing and decreasing flow and pressure than the blower, and because the oxygen valve is capable of providing a more precise control of flow and pressure than the blower.

Optionally, the method comprises the step of:
controlling the oxygen valve to deliver a flow of oxygen from the oxygen source to the inspiratory channel during the expiration phase, using the control unit.

In this way, the absence of flow produced by the blower can be compensated for during the expiration phase by providing an oxygen flow from the oxygen source. In particular, the inspiratory channel will be filled with oxygen during the expiration phase. In this way, an amount of oxygen will be present in the inspiratory channel upon the initiation of the subsequent inspiration phase, which potentially further can reduce consumption of oxygen by the breathing apparatus by delivering oxygen more efficiently. Still further, the delivery of a flow of oxygen from the oxygen source to the inspiratory channel during the expiration phase provides a bias flow, in the absence of a flow produced by the blower, which bias flow can be used to facilitate detection of a transition between the expiration phase and the inspiration phase. In this way, the Trigger Delay can be reduced.

Optionally, the method comprises the step of:
controlling the blower to deliver a flow of air to the inspiratory channel during the expiration phase, using the control unit.

In this way, the inspiratory channel will be filled with air during the expiration phase of the breathing cycle. As a result, a lung recruitment manoeuvre can be performed in the subsequent inspiration phase, using the oxygen valve, without subjecting the patient to an unnecessarily high concentration of oxygen.

Optionally, the breathing apparatus further comprises an input unit connected to the control unit, and wherein the method comprises the steps of:
employing the input unit to select a mode of operation among at least two different modes of operation, and
adapting the time period on the basis of the selected mode of operation.

In this way, a method is provided capable of adapting operation of a breathing apparatus in dependence of at least two different modes of operation.

According to a third aspect of this disclosure, the object is achieved by a computer program for performing a method of controlling operation of a breathing apparatus, wherein the computer program comprises computer readable code embedded in a control unit of the breathing apparatus and configured to cause the control unit to operate the breathing apparatus so as to perform the method according to embodiments described above. Since the computer program comprises computer readable code configured to cause the control unit to operate the breathing apparatus so as to perform the method according to embodiments of this disclosure, a computer program is provided overcoming, or at least alleviating, at least some of the above-mentioned problems and drawbacks. As a result, the above-mentioned object is achieved.

According to a fourth aspect of this disclosure, the object is achieved by a computer program product for performing a method of controlling operation of a breathing apparatus, wherein the computer program product comprises computer readable code embedded in a control unit of the breathing apparatus and configured to cause the control unit to operate the breathing apparatus so as to perform the method according to embodiments described above.

Because the computer program product comprises computer readable code configured to cause the control unit to operate the breathing apparatus so as to perform the method according to embodiments of this disclosure, a computer program product is provided overcoming, or at least alleviating, at least some of the above-mentioned problems and drawbacks. As a result, the above-mentioned object is achieved.

Further features of, and advantages achieved with, the embodiments of this disclosure will become apparent when studying the appended claims and the following detailed description.

BRIEF DESCRIPTION OF THE DRAWINGS

Various aspects of embodiments of the invention, including its particular features and advantages, will be readily understood from the example embodiments discussed in the following detailed description and the accompanying drawings, in which.

DETAILED DESCRIPTION

Aspects of embodiments of the present invention will now be described more fully. Like numbers refer to like elements throughout. Well-known functions or constructions will not necessarily be described in detail for brevity and/or clarity.

Figure 1:
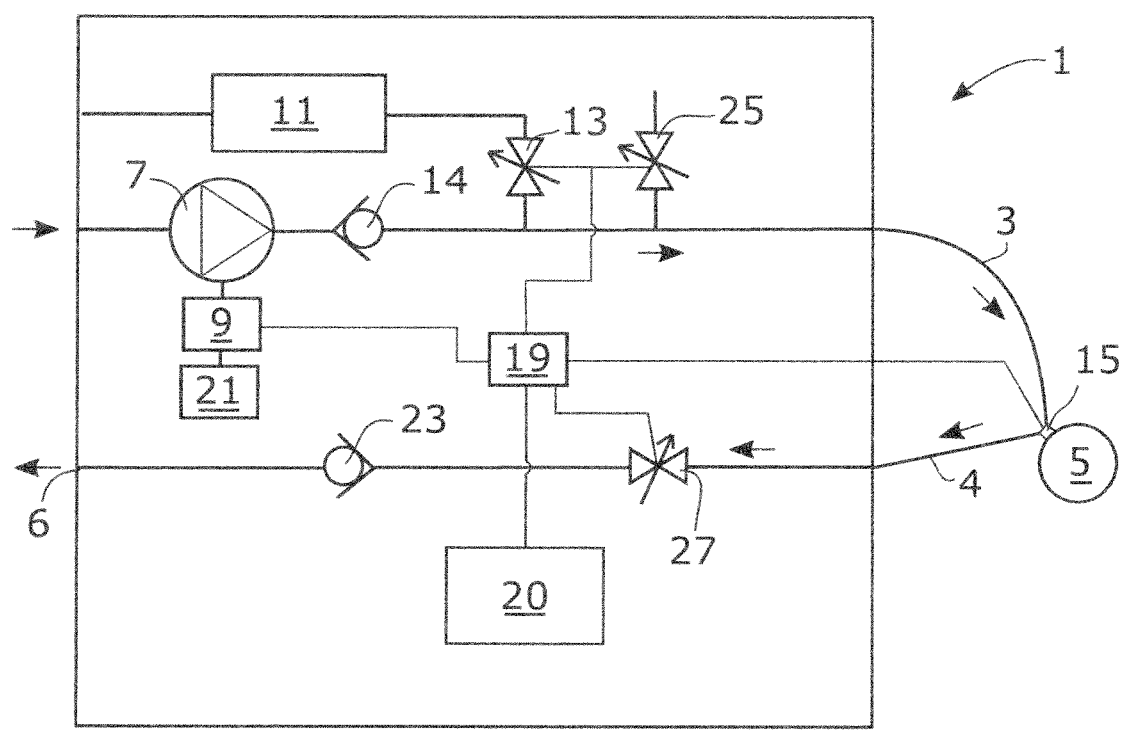
FIG. 1 illustrates a breathing apparatus, according to some embodiments.

FIG. 1 illustrates a breathing assistance apparatus 1 comprising an inspiratory channel 3, an expiratory channel 4 and a patient interface 5. The inspiratory channel 3 and the expiratory channel 4 are connected to the patient interface 5. The inspiratory channel 3 is configured to convey gas to the patient interface 5. The expiration channel 4 is arranged to convey gas from the patient interface 5 to an exhaust port 6 of the breathing assistance apparatus 1. The patient interface 5 may comprise a mask, endotracheal tube, tracheostomy tube, or the like. Further, the breathing apparatus 1 may comprise an y-piece connecting the inspiratory channel 3, the expiratory channel 4 and the patient interface 5. The breathing apparatus 1 further comprises a blower 7 comprising blower driving means 9. The blower 7 is arranged to produce a flow of ambient air to the inspiratory channel 3. The blower 7 may comprise a fan, a turbine, or the like, and is provided with a low flow resistance when not in operation. This in order to permit spontaneous breathing in case of a failure of the breathing assistance apparatus 1, so that the patient is able to inhale inter alia via the blower 7. The blower driving means 9 may comprise an electric motor arranged to drive the blower 7.

The breathing apparatus 1 further comprises an oxygen valve 13 arranged to be connected to a oxygen source 11. The oxygen valve 13 is configured to selectively deliver a flow of oxygen from the oxygen source 11 to the inspiratory channel 3. The oxygen source 11 may be a pressurized oxygen source. The oxygen source 11 may for example comprise a pressurizedoxygen bottle, an oxygen concentrator or a wall gas connection. The breathing apparatus 1 further comprises a valve 14, such as a check-valve, configured to prevent flow of gas in a direction from the patient interface 5 towards the blower 7 in the inspiratory channel 3. Thus, according to the illustrated embodiments, the valve 14 is arranged to only permit flow of air in a direction from the blower 7 towards the patient interface 5.

According to the embodiments illustrated in FIG. 1, the breathing apparatus 1 further comprises a second valve 23, in the form of a check valve, which is configured to prevent flow of gas in a direction from the exhaust port 6 towards the patient interface 5 in the expiratory channel 3. The breathing apparatus 1 further comprises a safety valve 25 and an expiratory valve 27. The safety valve 25 is arranged to limit maximum pressure in the inspiratory channel 3. The expiratory valve 27, which sometimes may be referred to as a positive end expiratory pressure (PEEP) valve, may be arranged to control the pressure in the expiratory channel 4.

Furthermore, the breathing apparatus 1 comprises a detecting unit 15 configured to detect breathing phases of a patient's breathing cycle. The breathing apparatus 1 further comprises a control unit 19 connected to the blower driving means 9, the oxygen valve 13 and the detecting unit 15. The detecting unit 15 may comprise one or more sensors arranged to sense pressure, and/or flow, in the inspiratory channel 3, and/or in the expiratory channel 4. The detecting unit 15 may comprise an Y-piece sensor arranged at a meeting point of the inspiratory channel 3 and the expiratory channel 4. The Y-piece sensor may measure flow, and/or pressure, in the inspiratory channel 3 and the expiratory channel 4 to sense breathing phases of a patient breathing through the patient interface 5. As an alternative, or in addition, the breathing assistance apparatus 1 may comprise a first sensor arranged to measure flow, and/or pressure, in the inspiratory channel 3 and a second sensor arranged to measure flow and/or pressure in the expiratory channel 4, where the first and second sensors are connected to the control unit 19. According to such embodiments, the breathing phases of a patient breathing through the patient interface 5 may be sensed by using signals from the first and second sensors. Furthermore, the detecting unit 15 may comprise one or more external sensors, such as one or more sensors attached to the patient for detecting breathing phases of the patient's breathing cycles, for example one or more diaphragm activity sensors. The detection of breathing phases may encompass detection of initiation of inspiration phases and expiration phases, as well as progress of the inspiration phases and the expiration phases. Progress of the inspiration phases and the expiration phases may encompass volume of gas delivered to the patient interface, and volume of gas conveyed from the patient interface, and/or volume of gas delivered to the patient interface in relation to a current patient tidal volume, and volume of gas conveyed from the patient interface in relation a to current patient tidal volume, and/or progress thereof regarding duration of inspiration phases and duration of expiration phases.

According to the illustrated embodiments, the breathing apparatus 1 comprises one or more batteries 21 connected to the blower driving means 9 to supply driving energy to the blower driving means 9.

The control unit 19 is configured to control the blower driving means 9 so that the blower 7 produces essentially or substantially no flow of air to the inspiratory channel 3 during a time period starting after 30% of a duration of an inspiration phase 16. The controlling of the blower driving means 9 may encompass a reduction in operational rate, e.g. rotational velocity, of the blower 7 so that the blower 7 produces essentially or substantially no flow of air to the inspiratory channel 3 during the time period. Thus, a reduction in operational rate of the blower driving means 9 may be performed such that the pressure obtained by the blower 7 is essentially or substantially equal to a counter pressure in the inspiratory channel 3. As a result, the blower 7 will produce essentially or substantially no flow of air to the inspiratory channel 3. According to further embodiments, the control unit 19 is configured to deactivate the blower driving means 9 during the time period, so that the blower 7 produces essentially or substantially no flow of air to the inspiratory channel 3 during the time period. The control unit 19 may control the blower driving means 9 so that the blower 7 produces a flow of air to the inspiratory channel 3 up to the start of the time period, and after the end of the time period.

Further features and advantages of the present disclosure will be explained with reference to the FIGS. 2-6.

Figure 2:
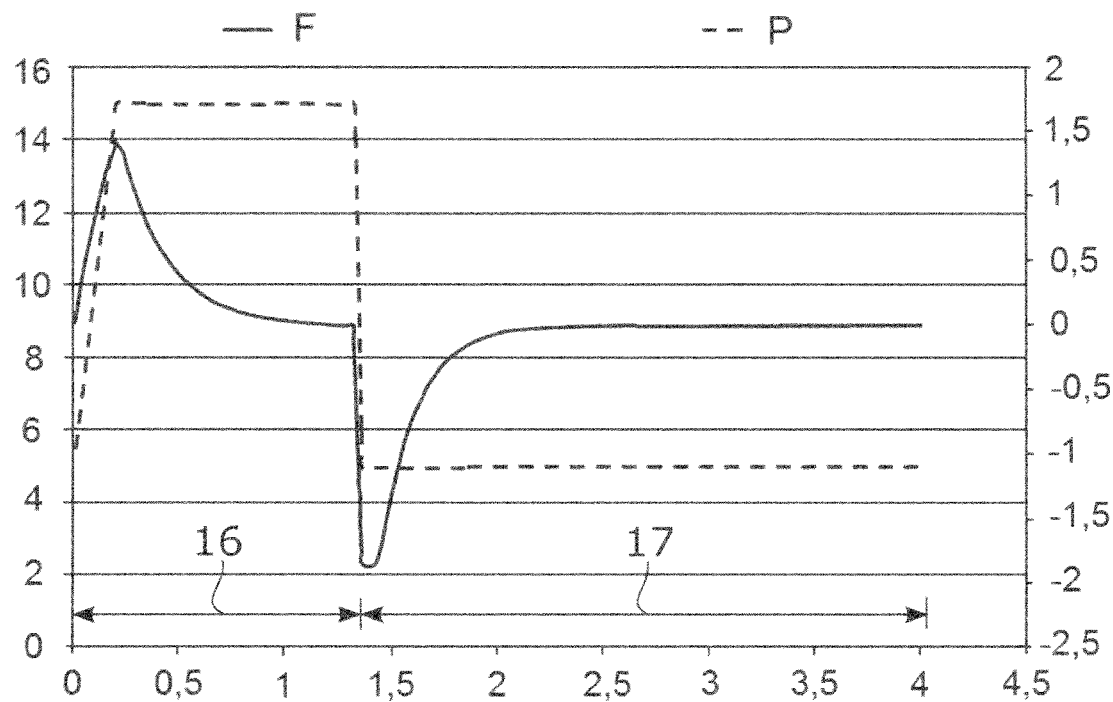
FIG. 2 illustrates a graph showing an example of a normal breathing pattern (i.e. one breathing cycle) for an adult patient.

FIG. 2 illustrates a graph showing an example of a normal breathing pattern for an adult patient. The solid line corresponds to the flow F, and the dashed line corresponds to the pressure P, during an inspiration phase 16 followed by an expiration phase 17. The numbers at the vertical line to the left in the graph of FIG. 2 indicates the pressure P in hectopascal hPa, whereas numbers at the vertical line to the right in the graph indicates the Flow F in litre per second LPS, and the numbers at the horizontal line in the graph indicates time in seconds.

Figure 3:
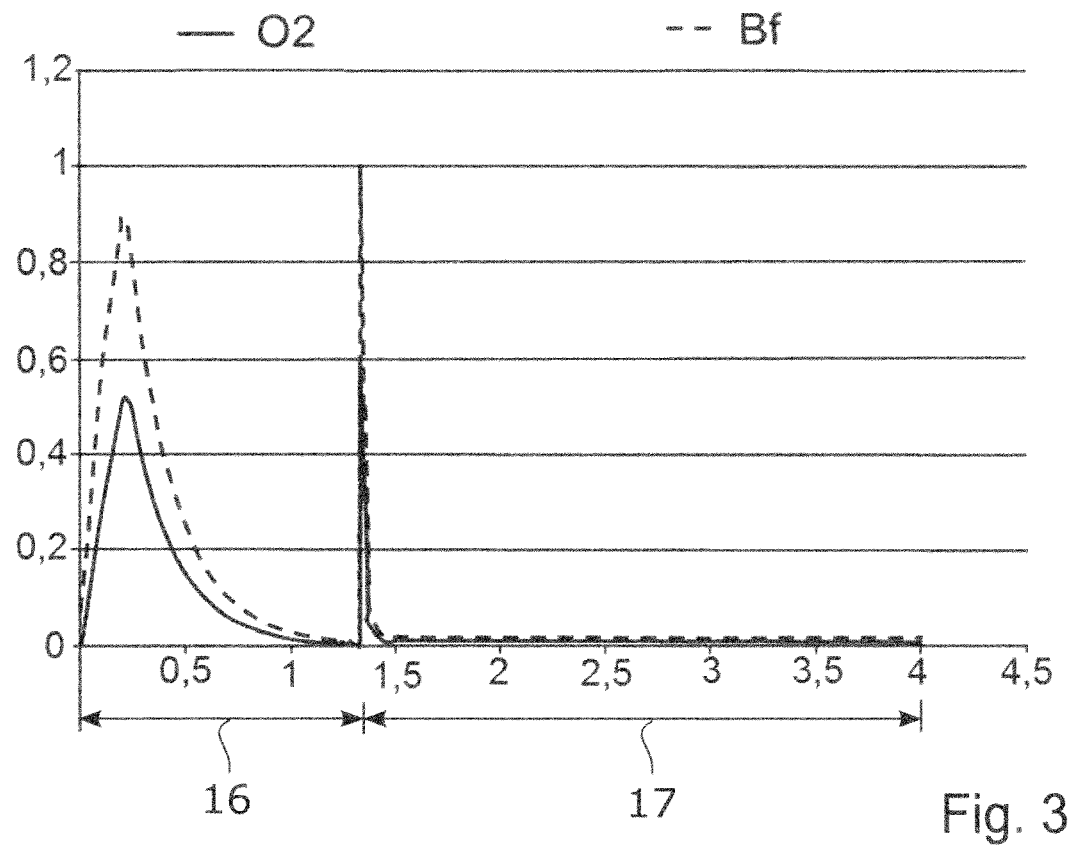
FIG. 3 illustrates a graph showing normal flow from a blower and oxygen valve of a breathing apparatus.

In the illustrated example, the duration of the breath is approximately 4 seconds, in which the duration of the inspiration phase 16 is approximately 1.4 seconds and the duration of the subsequent expiration phase 17 is approximately 2.6 seconds. A duration of a breath being approximately 4 seconds gives a respiration rate of approximately 15 breaths per minute, which can be considered normal for a healthy adult patient. Obviously, the respiration rate, as well as the duration of the inspiration phase 16 and the expiration phase 17, may vary to a great extent, and embodiments of this disclosure are not limited to a particular respiration rate. As examples, during rest, a normal healthy adult patient usually breathes with a respiration rate of 15 to 20 breaths per minute, whereas new-borns may breathe with a respiration rate of up to 60 breaths per minute. Further, the physical state of the patient significantly affects the respiration state. FIG. 3 illustrates a graph showing normal flow Bf from a blower and normal flow O2 from an oxygen valve of a breathing apparatus. The solid line corresponds to the flow O2 from the oxygen valve, and the dashed line corresponds to the flow Bf from the blower, during an inspiration phase 16 followed by an expiration phase 17. The numbers at the vertical line to the left in the graph of FIG. 3 indicates Flow in litre per second LPS, and the numbers at the horizontal line in the graph indicates time in seconds.

As is evident from the graph of FIG. 3, a sudden increase in flow is obtained during the onset of the expiration phase 17. This is caused by the fact that the blower is slow in decreasing rotational velocity and thus also slow in reducing the pressure and flow produced during the inspiration phase 16. Further, as shown in FIG. 3, to maintain an essentially constant oxygen concentration, the flow from the oxygen valve follows the flow from the blower, which further increases the flow obtained during the onset of the expiration phase 17. Accordingly, the flow of air in the inspiratory channel during an inspiration phase 16 will continue into a portion of an expiration phase 17. A patient is, as a result thereof, subjected to a flow of air in the inspiratory channel, when the patient is about to exhale. Such a flow of air is unwanted, increases work of breathing and may be inconvenient or uncomfortable for the patient. In addition, such a flow of air may increase consumption of oxygen by the breathing apparatus.

Figure 4:
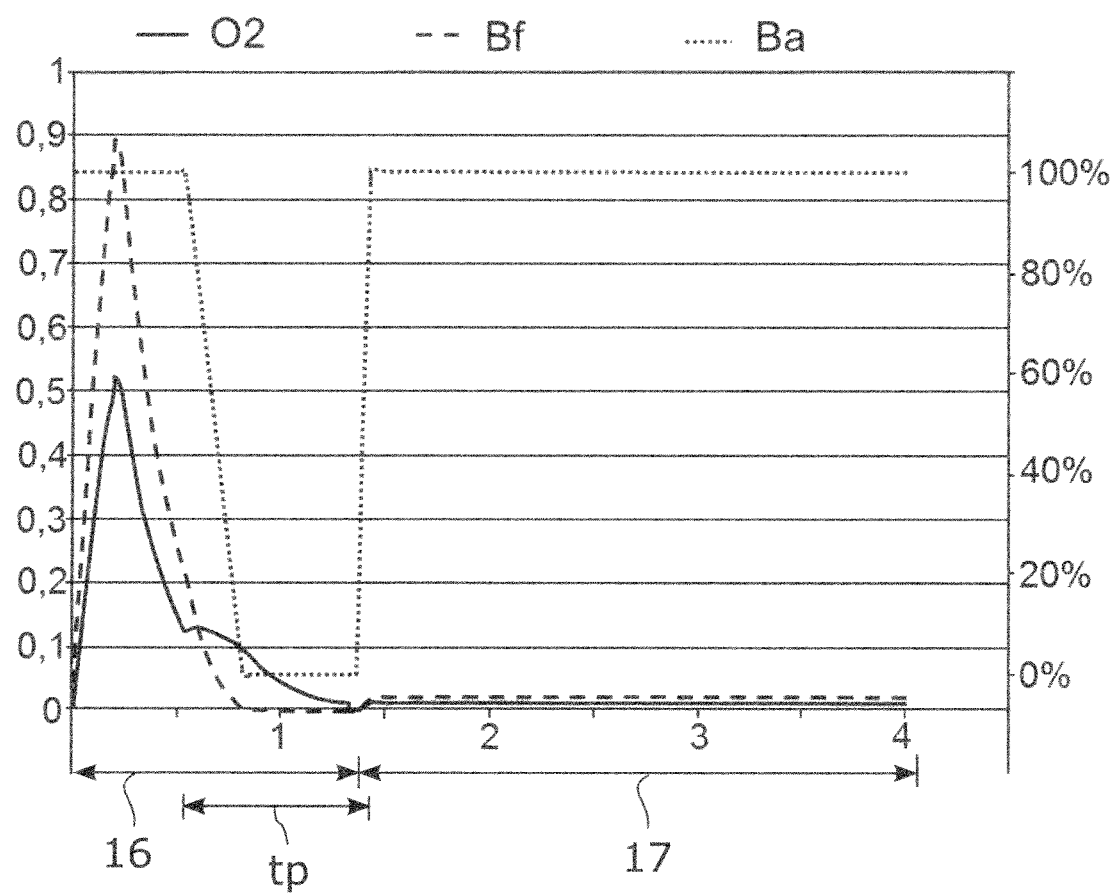
FIG. 4 illustrates a graph showing a first mode of operation, according to some embodiments of the breathing apparatus illustrated in FIG. 1.

FIG. 4 illustrates a graph showing a first mode of operation, according to some embodiments of this disclosure, of the breathing apparatus 1 illustrated in FIG. 1. Therefore, below, reference is made to FIG. 1, as well as FIG. 4. In FIG. 4, the solid line corresponds to the flow O2 from the oxygen valve 13, the dashed line corresponds to the flow Bf from the blower 7, and the dotted line corresponds to the percentage of blower activity Ba compared to a normal blower activity, during an inspiration phase 16 followed by an expiration phase 17. The numbers at the vertical line to the left in the graph of FIG. 4 indicates the flow of oxygen O2 from the oxygen valve 13 in litre per second LPS, the numbers at the horizontal line in the graph indicates time in seconds, and the numbers at the vertical line to the right in the graph indicates percentage of blower activity Ba compared to a normal continuous operation of the blower 7.

The control unit 19 of the breathing apparatus 1 is configured to control the blower driving means 9 so that the blower 7 produces essentially or substantially no flow of air to the inspiratory channel 3 during a time period tp. The term "time period tp" as used herein, may also be referred to as the "transitional time period tp". The controlling of the blower driving means 9 so that the blower 7 produces essentially or substantially no flow of air to the inspiratory channel 3 during the time period tp may encompass a deactivation of the blower driving means 9 or a reduction in operation rate of the blower driving means 9, so that the blower 7 produces essentially or substantially no flow of air to the inspiratory channel 3. In this context, the phrase "substantially no flow of air to the inspiratory channel during time period tp" should be construed with respect to FIG. 4.

According to the non-limiting embodiments illustrated in FIG. 4, the duration of the inspiration phase 16 is approximately 1.4 seconds and the duration of the expiration phase 17 is approximately 2.6 seconds. The time period tp starts 0.52 seconds into the inspiration phase 16. Thus, according to the illustrated embodiments, the time period tp starts at approximately 37% of the duration of the inspiration phase 16.

Furthermore, according to the illustrated embodiments, the time period tp ends 0.05 seconds into the expiration phase 17. Thus, according to the illustrated embodiments, the time period tp ends at approximately 2% of the duration of the expiration phase 17. The time period tp thus starts during the inspiration phase 16 and ends during the subsequent expiration phase 17, meaning that the time period tp lasts over the transitioning area between the inspiration phase 16 and the expiration phase 17. Furthermore, since the time period tp starts at approximately 37% of the duration of the inspiration phase 16, the blower 7 will have plenty of time to reduce its rotational velocity and, thus, also reduce the flow of air produced to the inspiratory channel 3. As a result, the increase in flow normally obtained in the inspiratory channel 3 during an onset of the expiration phase 17, as is illustrated in FIG. 3 is eliminated, or at least significantly reduced. Thereby, the flow of gas that normally is flowing towards the patient in the inspiratory channel 3, when the patient is about to exhale is eliminated, or at least significantly reduced, which provides conditions for a reduced consumption of oxygen. Furthermore, the combined flow from the inspiratory channel 3 and the expiratory flow from the patient in the expiratory channel 4 is reduced, which reduces the flow resistance in the expiratory channel 4, thus reducing the work of breathing. In addition, because the control unit 19 is configured to control the blower driving means 9 so that the blower 7 produces essentially or substantially no flow of air to the inspiratory channel 3 during the time period tp, the energy consumption of the breathing apparatus 1 is reduced and the life length of the blower 7 is increased.

According to some embodiments of the first mode of operation, the time period tp may start during a final portion of the inspiration phase 16 and end during an onset of the expiration phase 17. Thereby, energy consumption of the breathing apparatus 1 is reduced, the increase in flow normally obtained in the inspiratory channel during an onset of the expiration phase, as illustrated in FIG. 3 is eliminated, or at least significantly reduced, which improves work of breathing and provides conditions for a reduced consumption of oxygen.

According to the illustrated embodiments of this disclosure, the control unit 19 is configured to control the oxygen valve 13 to increase delivered flow of oxygen from the oxygen source 11 to the inspiratory channel 3 during an initial portion of the time period tp. As a result, the absence of flow of air produced by the blower 7 is compensated for with oxygen flow during the initial portion of the time period tp. According to some embodiments, the control unit 19 is configured to control the oxygen valve 13 to increase delivered flow of oxygen from the oxygen source 11 to the inspiratory channel 3 during a final portion of the inspiration phase 16. In this way, the absence of flow produced by the blower 7 in the final portion of the inspiration phase is compensated for with a flow of oxygen from the oxygen source 11. The control unit 19 may be configured to control the oxygen valve 13 to increase delivered flow of oxygen from the oxygen source 11 to the inspiratory channel 3 during at least a portion of the time period tp, or during essentially or substantially the entire time period tp, to compensate for the absence of flow produced by the blower 7.

By compensating the absence of flow from the blower 11 with a flow of oxygen from the oxygen source 11, the rise and fall times can be significantly improved since the oxygen valve 13 is much quicker in increasing and decreasing flow and pressure than the blower 7. Also, the pressure time product can be improved because the oxygen valve 13 is much quicker in increasing and decreasing flow and pressure than the blower 7, and since the oxygen valve 13 is capable of providing a more precise control of flow and pressure than the blower 7.

Accordingly, a breathing apparatus 1 is provided capable of improving performance, while the energy consumption is reduced and the life length of the blower 11 is increased.

As mentioned above, according to the embodiments illustrated in FIG. 4, the time period tp ends at approximately 2% of the duration of the expiration phase 17, meaning that the control unit 19, according to these embodiments, is configured to control the blower driving means 9 so that the blower 7 starts to produce a flow of air to the inspiratory channel 3 in an initial portion of the expiration phase 17. The time period tp may end approximately 100 ms into the expiration phase 17. Furthermore, the flow produced by the blower 7 continues during essentially the entire expiration phase 17. As a result, work of breathing is improved and a bias flow is provided which can be utilized by the detecting unit 15, to facilitate detection of a transition between the inspiration phase 16 and the expiration phase 17. In this way, the Triger Delay can be reduced. As is evident from FIG. 4, the flowrate produced by the blower 7 during the expiration phase 17 is much lower than during the inspiration phase 16, which can be seen by the dashed line showing the flow Bf from the blower 7. As mentioned above, the dotted line corresponds to the percentage of blower activity Ba compared to a normal blower activity, which normal blower activity is much lower during the expiration phase 17 than during the inspiration phase 16.

According to some embodiments of this disclosure, the control unit 19 is configured to control the oxygen valve 13 to deliver a flow of oxygen from the oxygen source 11 to the inspiratory channel 3 from an onset of the inspiration phase 16 to 40%-100% of the duration of the inspiration phase 16. If a need arises to produce a pressure that is higher, and/or a need arises to produce faster inspiratory rise time than can be produced by the blower 7, the oxygen valve 13 can be used when connected to a pressurized oxygen source. In this way, the absence of sufficient flow from the blower 7 is compensated for by oxygen flow from the oxygen source 11 during a great proportion of the inspiration phase 16. According to some embodiments, the control unit 19 is configured to control the oxygen valve 13 to deliver a flow of oxygen from the oxygen source 11 to the inspiratory channel 3 from an onset of the inspiration phase 16 to 100% of the duration of the inspiration phase 16, i.e. to the end of the inspiration phase 16. Furthermore, according to such embodiments, the breathing apparatus 1 can be used to perform a lung recruitment manoeuvre, even in cases where the blower 7 is producing an insufficient flow of air to the inspiratory channel 3, to reach higher recruitment pressures.

Optionally, the control unit 19 is configured to control the blower 7 to deliver a flow of air to the inspiratory channel 3 during the expiration phase 17. In this way, the inspiratory channel 3 will be filled with air during the expiration phase 17. The flow of air to the inspiratory channel 3 during the expiration phase 17 and the dimensions of the inspiratory channel 3, such as the length and the inner diameters of the inspiratory channel 3, may be adapted such that the inspiratory channel 3 is filled with a predetermined volume of air during the expiration phase 17. Then, in the subsequent inspiration phase 16, a lung recruitment manoeuvre can be performed by delivering a flow of oxygen from the oxygen source 11 to the inspiratory channel 3, using the oxygen valve 13. In this way, the predetermined volume of air in the inspiratory channel 3 will be pushed by the flow delivered from the oxygen valve 13. As a result, a lung recruitment manoeuvre can be performed in the subsequent inspiration phase 16 in a controlled manner, using the oxygen valve 13, without subjecting the patient to an unnecessarily high concentration of oxygen.

Figure 5:
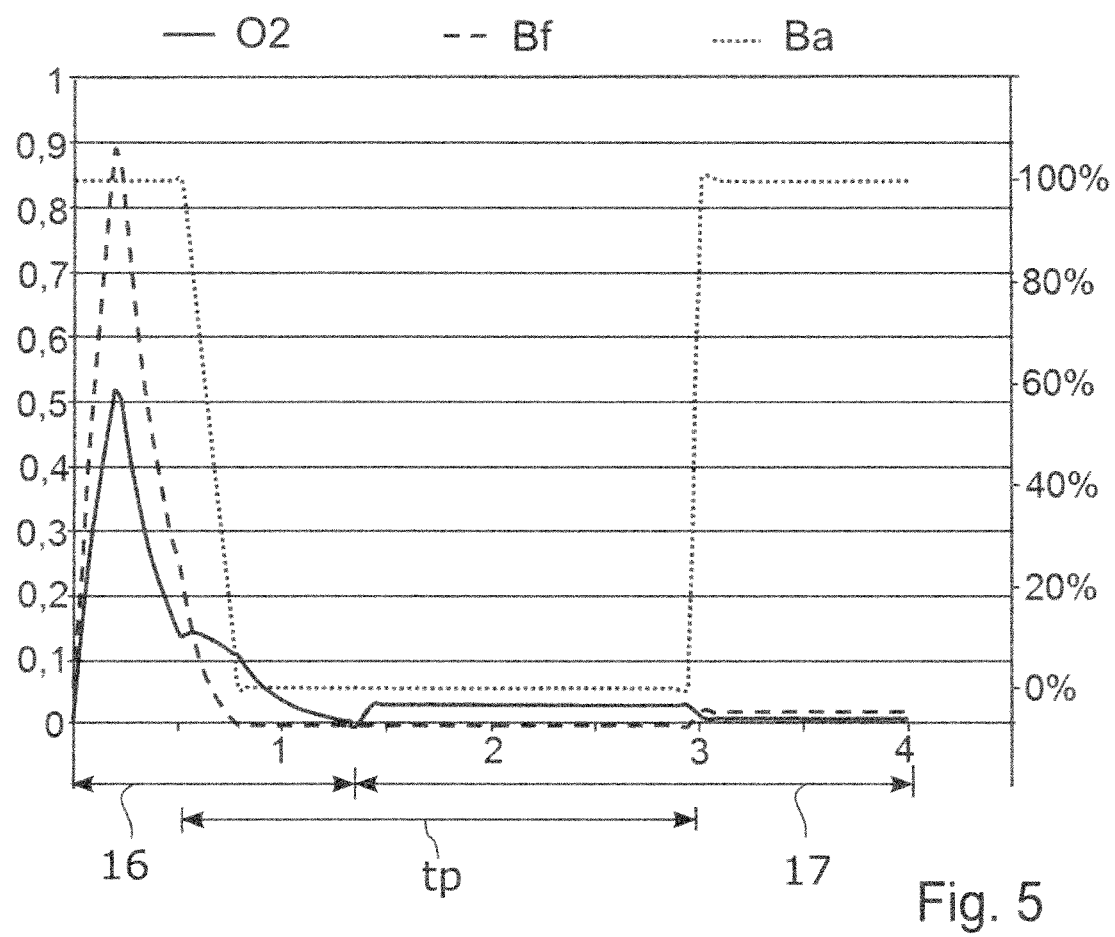
FIG. 5 illustrates a graph showing a second mode of operation, according to some embodiments of the breathing apparatus illustrated in FIG. 1.

FIG. 5 illustrates a graph showing a second mode of operation, according to some embodiments of this disclosure, of the breathing apparatus 1 illustrated in FIG. 1. Therefore, below, reference is made to FIG. 1 as well as FIG. 5. In FIG. 5, the solid line corresponds to the flow O2 from the oxygen valve 13, the dashed line corresponds to the flow Bf from the blower 7, and the dotted line corresponds to the percentage of blower activity Ba compared to a normal blower activity, during an inspiration phase 16 followed by an expiration phase 17. The numbers at the vertical line to the left in the graph of FIG. 5 indicates the flow of oxygen O2 from the oxygen valve 13 in litre per second LPS, the numbers at the horizontal line in the graph indicates time in seconds, and the numbers at the vertical line to the right in the graph indicates percentage of blower activity Ba compared to a normal continuous operation of the blower 7.

Like the embodiments of FIG. 4, the duration of the inspiration phase 16 is approximately 1.4 seconds and the duration of the expiration phase 17 is approximately 2.6 seconds, although this is for illustrative purposes only and should not be construed as limiting. Also, like the embodiments of FIG. 4, the time period tp starts 0.52 seconds into the inspiration phase 16, in accordance with a non-limiting embodiment. Thus, also according to the non-limiting embodiments of the second mode of operation illustrated in FIG. 5, the time period tp starts at approximately 37% of the duration of the inspiration phase 16.

According to the non-limiting embodiments illustrated in FIG. 5, the time period tp ends approximately 1.5 seconds into the subsequent expiration phase 17. Thus, the time period tp ends at approximately 57% of the duration of the expiration phase 17, in accordance with a non-limiting embodiment. As a result, the energy consumption of the breathing apparatus 1 is further reduced and the life length of the blower 7 is further increased, as compared to the first mode of operation, because the control unit 19 is controlling the blower driving means 9 so that the blower 7 produces essentially or substantially no flow of air to the inspiratory channel 3 during a longer time period tp, in the second mode of operation than in the first mode of operation.

In addition, also in the second mode of operation, the time period tp starts during the inspiration phase 16 and ends during the subsequent expiration phase 17, meaning that the time period lasts over the transitioning area between the inspiration phase 16 and the expiration phase 17. Thus, also in the second mode of operation, the increase in flow normally obtained in the inspiratory channel 3 during an onset of the expiration phase 17 is eliminated, or at least significantly reduced, which improves work of breathing and provides conditions for a reduced consumption of oxygen by delivering oxygen more efficiently.

Furthermore, in the second mode of operation illustrated in FIG. 5, the control unit 19 is configured to control the oxygen valve 13 to deliver a flow of oxygen from the oxygen source 11 to the inspiratory channel 3 in the portion of the time period tp extending into the subsequent expiration phase 17. As a result, the absence of flow produced by the blower 7 is compensated for also during this portion of the subsequent expiration phase 17 and the delivered flow of oxygen from the oxygen source 11 provides a bias flow during this portion of the expiration phase 17. In addition, the inspiratory channel 3 will be filled with oxygen during the expiration phase 17. Consequently, an amount of oxygen will be in the inspiratory channel 3 upon the initiation of the subsequent inspiration phase 16, which can reduce the consumption of oxygen. This occurs because when a patient inhales and exhales, in principle, only the first 75% of the breath is actually used for transporting oxygen to the patient and carbon dioxide from the patient. By increasing the amount of oxygen delivered to the patient during the first phase of inspiration, the oxygen consumption can be significantly reduced because less oxygen is delivered during portions of the breathing cycle that are not responsible for respiration. During high leakage situations, the effect is even stronger. Still, the amount of oxygen delivered to the patient can be controlled to a pre-set value by controlling the amount of oxygen delivered to the patient during the first phase of inspiration.

Furthermore, by compensating the absence of flow from the blower 7 with a flow of oxygen from the oxygen source 11, the performance of the breathing apparatus 1 can be improved. This occurs because the rise and fall times, and the pressure time product, can be improved since the oxygen valve 13 is much quicker in increasing and decreasing flow and pressure than the blower 7, and because the oxygen valve 13 is capable of providing a more precise control of flow and pressure than the blower 7.

Figure 6:
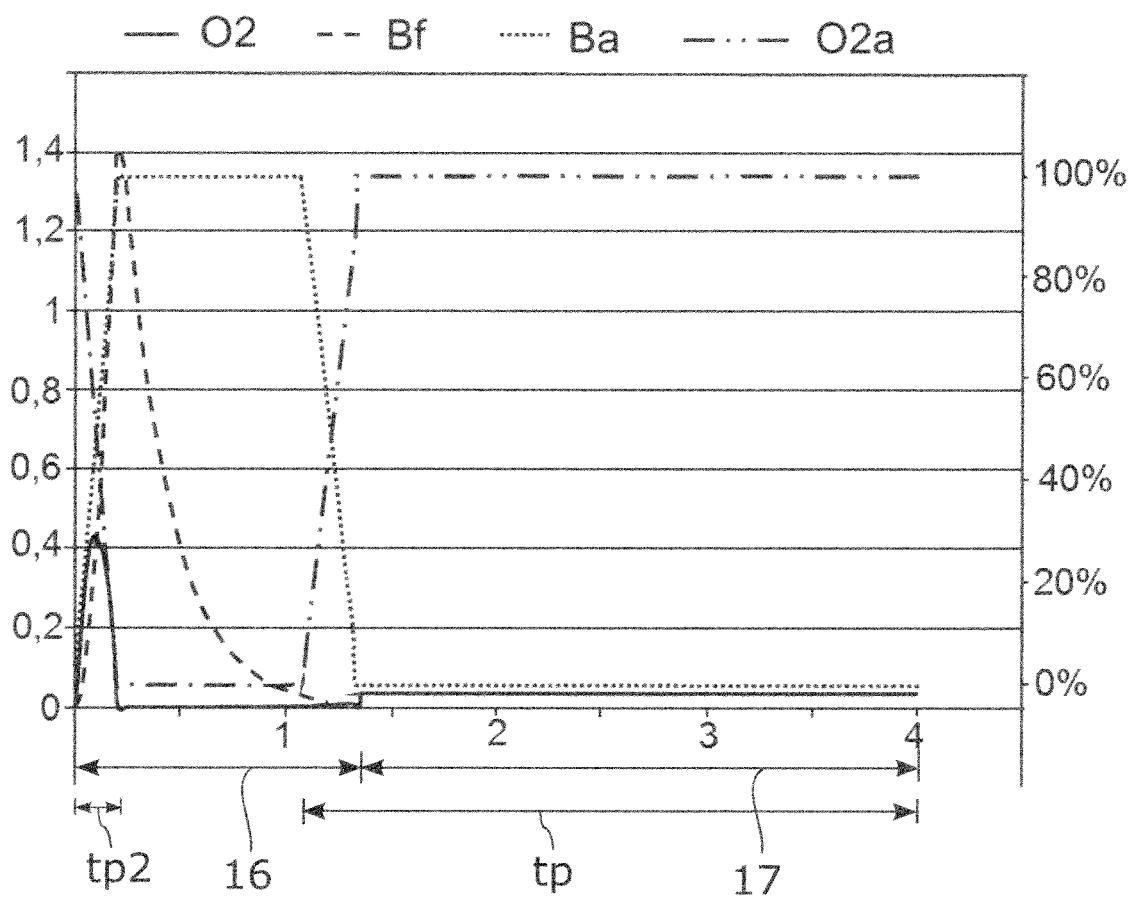
FIG. 6 illustrates a graph showing a third mode of operation, according to some embodiments of the breathing apparatus illustrated in FIG. 1.

FIG. 6 illustrates a graph showing a third mode of operation, according to some embodiments of this disclosure, of the breathing apparatus illustrated in FIG. 1. Therefore, below, reference is made to FIG. 1 as well as FIG. 6. In FIG. 6, the solid line corresponds to the flow O2 from the oxygen valve 13, the dashed line corresponds to the flow Bf from the blower 7, the dotted line corresponds to the percentage of blower activity Ba compared to a normal blower activity, and the broken line corresponds to the oxygen activity O2 a during an inspiration phase 16 followed by an expiration phase 17. The numbers at the vertical line to the left in the graph of FIG. 6 indicates the flow of oxygen O2 from the oxygen valve 13 in litre per second LPS, the numbers at the horizontal line in the graph indicates time in seconds, and the numbers at the vertical line to the right in the graph indicates percentage of blower activity Ba compared to a normal continuous operation of the blower 7, as well as percentage of oxygen activity O2 a.

The duration of the inspiration phase 16 is approximately 1.4 seconds and the duration of the subsequent expiration phase 17 is approximately 2.6 seconds, like the non-limiting embodiments of FIG. 4 and FIG. 5. According to the third mode of operation, the time period tp starts during a final portion of the inspiration phase 16. The final portion of the inspiration phase 16 may be between 65% and 95% of the duration of the inspiration phase 16. According to the illustrated embodiments, the time period tp starts approximately 1 second into the inspiration phase 16. Thus, according to the illustrated embodiments, the time period tp starts at approximately 75% of the duration of the inspiration phase 16. According to the illustrated embodiments, the time period tp last during the entire expiration phase 17 and ends upon initiation of the subsequent inspiration phase 16. Thus, also in the third mode of operation, the time period tp lasts over the transitioning area between the inspiration phase 16 and the expiration phase 17. Accordingly, also in the third mode of operation, the increase in flow normally obtained in the inspiratory channel 3 during an onset of the expiration phase 17 is eliminated, or at least significantly reduced, which improves work of breathing and provides conditions for a reduced consumption of oxygen by the breathing apparatus.

According to further non-limiting embodiments of the third mode of operation, the time period tp may end during 50%-75% of the duration of the expiration phase 17.

According to the non-limiting embodiments of the third mode of operation illustrated in FIG. 6, the control unit 19 is configured to control the oxygen valve 13 to increase delivered flow of oxygen from the oxygen source 11 to the inspiratory channel 3 during an initial portion of the inspiration phase 16. According to some non-limiting embodiments, the control unit 19 is configured to control the oxygen valve 13 to deliver a flow of oxygen from the oxygen source 11 to the inspiratory channel 3 during a second time period tp2 lasting from the onset of the inspiration phase 16 to 10%-30% of the duration of the inspiration phase 16. According to the illustrated non-limiting embodiments, the second time period tp2 lasts from the onset of the inspiration phase 16 to 14% of the duration of the inspiration phase 16. Furthermore, according to the illustrated embodiments, the control unit 19 is configured to control the oxygen valve 13 to not deliver any flow of oxygen from the oxygen source 11 to the inspiratory channel 3 in the remaining portion of the inspiration phase 16. Thus, according to the non-limiting illustrated embodiments, the control unit 19 is configured to control the oxygen valve 13 to only deliver a flow of oxygen from the oxygen source 11 to the inspiratory channel 3 during the second time period tp2 in the inspiration phase 16. In this way, the consumption of oxygen can be significantly reduced increasing the efficiency of oxygen delivery. This occurs because when a patient inhales and exhales, in principle, only the first 75% of the breath is used for transporting oxygen to the patient and carbon dioxide from the patient. By only delivering oxygen to the patient during the first phase of the inspiration phase 16, the oxygen consumption will be drastically reduced. During high leakage situations, the effect will be even stronger.

Furthermore, by delivering a flow of oxygen from the oxygen source 11 to the inspiratory channel 3 during an initial portion of the inspiration phase 16, the rise time of the pressure in the inspiratory channel 3 is reduced. This occurs because the oxygen valve 13 is much quicker in achieving a pressure than the blower 7. Thus, the performance of the breathing apparatus 1 is increased. Furthermore, the pressure time product can be improved since the oxygen valve 13 is much quicker in increasing and decreasing flow and pressure than the blower 7, and because the oxygen valve 13 is capable of providing a more precise control of flow and pressure than the blower 7.

In addition, in the third mode of operation illustrated in FIG. 6, the control unit 19 is configured to control the oxygen valve 13 to deliver a flow of oxygen from the oxygen source 11 to the inspiratory channel 3 during the expiration phase 17. As a result, the absence of flow produced by the blower 7 is compensated for by oxygen flow from the oxygen source 11 during the expiration phase 17. Also, the inspiratory channel 3 will be filled with oxygen during the expiration phase 17 and an amount of oxygen will thereby be present in the inspiratory channel 3 upon the initiation of the subsequent inspiration phase 16. As a result, the consumption of oxygen can be even further reduced. In addition, the delivering of a flow of oxygen from the oxygen source 11 to the inspiratory channel 3 during the expiration phase 17 provides a bias flow, in the absence of a flow produced by the blower 7. The bias flow can be utilized by the detecting unit 15, to facilitate detection of a transition between the inspiration phase 16 and the expiration phase 17. In this way, the Trigger Delay can be reduced To summarize, in accordance with the above disclosure, the control of the breathing apparatus 1 can be performed in an optimized manner regarding different aspects, as shown herein, by using the blower 7 and the oxygen valve 13 in a manner in which they are the most efficient. In addition, a breathing apparatus 1 is provided capable of operating in different modes of operation comprising modes of operation appropriate for different situations. Among the modes of operation described herein, the consumption of oxygen is the lowest in the third mode of operation illustrated in FIG. 6, followed by the second mode of operation illustrated in FIG. 5, and then the first mode of operation illustrated in FIG. 4, with small differences between the second and third modes of operation.

The consumption of energy and the life length of the blower 7 is the lowest in the second mode of operation illustrated in FIG. 5, followed by the first mode of operation illustrated in FIG. 4, and then the third mode of operation illustrated in FIG. 6.

The performance of the breathing apparatus 1 is the best in in the first mode of operation illustrated in FIG. 3, followed by the third mode of operation illustrated in FIG. 6, and then the second mode of operation illustrated in FIG. 6.

According to some embodiments of this disclosure, the time period tp may start after 30% of a duration of an inspiration phase 16 and may end prior to 75% of a duration of the subsequent expiration phase 17. According to further embodiments, the control unit 19 is configured to initiate the time period tp after 50% of a tidal volume of the patient has been delivered to the patient interface 5, and to end the time period tp before 75% of the tidal volume of the patient has been conveyed from the patient interface 5.

According to the embodiments of the breathing apparatus 1 illustrated in FIG. 1, the breathing apparatus 1 further comprises an input unit 20 connected to the control unit 19. The input unit 20 is configured to provide selection of a mode of operation among at least two different modes of operation. The input unit 20 may comprise a touch sensitive screen, one or more buttons, one or more knobs, a mouse, a trackball, or the like, configured to provide selection of a mode of operation.

The control unit 19 may adapt the time period tp, the control of the blower driving means 7, and/or control of the oxygen valve 13 on the basis of the selected mode of operation.

According to some embodiments of this disclosure, the input unit 20 is configured to provide selection of a mode of operation among the first mode, the second mode and the third mode of operation described herein. In this way, a user of the breathing apparatus 1 may select a mode of operation in dependence of a current situation and in dependence of a wanted performance of the breathing apparatus 1. As an example, in case of a low energy level of the batteries 21 of the breathing apparatus 1, a user may select the second mode of operation illustrated in FIG. 5 in which the consumption of energy is the lowest among the first, the second and the third modes of operation. Furthermore, in case the user wants to use oxygen sparingly, for example in cases where the oxygen source is a pressurized oxygen bottle, the user may select the third mode of operation illustrated in FIG. 6, in which consumption of oxygen is the lowest among the first, the second and the third mode of operation. Still further, if the user wants to optimize performance of the breathing apparatus 1, the user may select the first mode of operation illustrated in FIG. 3, which gives the best performance among the first, the second and the third mode of operation.

According to still further embodiments, the control unit 19 may be adapted to select a mode of operation, among at least two different modes of operation, on the basis of the energy status of the one or more batteries 21, and/or on the basis of a level of oxygen in the oxygen source 11. In this way, a breathing apparatus 1 is provided capable of automatically adapting to a current situation.

Furthermore, additional, and/or different, operational modes than the first, the second and the third operational mode described herein may be utilized without departing from the scope of the described embodiments of this disclosure, as defined by the appended claims. In addition, gradual or stepwise transitions between different operational modes may be performed.

Figure 7:
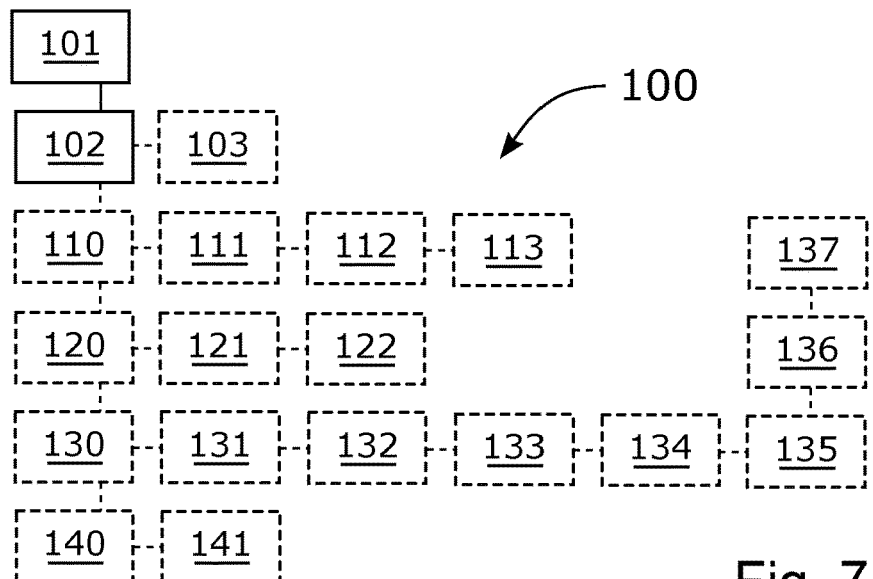
FIG. 7 illustrates a method of controlling a breathing apparatus.

FIG. 7 illustrates a method 100 of controlling a breathing apparatus. The breathing apparatus may be a breathing apparatus 1 as is illustrated in FIG. 1, and some of the features and advantages of the breathing apparatus 1 and the method 100 are explained with reference to FIG. 2-FIG. 6. Therefore, below, reference is made to FIG. 7 as well as to FIG. 1-FIG. 6. The method 100 is a method 100 of controlling a breathing apparatus 1, wherein the breathing apparatus 1 comprises:

an inspiratory channel 3, an expiratory channel 4 and a patient interface 5, wherein the inspiratory channel 3 and the expiratory channel 4 are connected to the patient interface 5, a blower 7 comprising blower driving means 9, wherein the blower 7 is arranged to produce a flow of air to the inspiratory channel 3, an oxygen valve 13 connected to a oxygen source 11, wherein the oxygen valve 13 is configured to selectively deliver a flow of oxygen from the oxygen source 11 to the inspiratory channel 3, a valve 14 configured to prevent flow of gas in a direction from the patient interface 5 in the inspiratory channel 3, a detecting unit 15 configured to detect breathing phases 16, 17, and a control unit 19 connected to the blower driving means 9, the oxygen valve 13 and the detecting unit 15.

As illustrated in FIG. 7, the method 100 comprises the steps of:

detecting 101 breathing phases 16, 17, using the detecting unit 15, and controlling 102 the blower driving means 9, using the control unit 19, so that the blower 7 produces essentially or substantially no flow of air to the inspiratory channel 3 during a time period tp starting after 30% of a duration of an inspiration phase 16 and ending the latest upon initiation of the subsequent inspiration phase 16.

As illustrated in FIG. 7, the method 100 may comprise the step of:

deactivating 103 the blower driving means 9 during the time period tp, using the control unit 19.

As illustrated in FIG. 7, the method 100 may comprise the steps of:

starting 110 the time period tp during the inspiration phase 16, and ending 120 the time period tp during the subsequent expiration phase 17. The starting 110 and the ending 120 of the time period tp may be performed using the control unit 19.

As illustrated in FIG. 7, the method 100 may comprise the steps of:

starting 111 the time period tp during a final portion of the inspiration phase 16, and ending 121 the time period tp during an onset of the subsequent expiration phase 17. The starting 111 and the ending 121 of the time period tp may be performed using the control unit 19.

As illustrated in FIG. 7, some embodiments of the method 100 may comprise the steps of:

starting 112 the time period tp during a final portion of the inspiration phase 16, and ending 122 the time period tp during 50%-75% of a duration of the subsequent expiration phase 17. The starting 112 and the ending 122 of the time period tp may be performed using the control unit 19.

According to some embodiments, the final portion of the inspiration phase 16 is between 65% and 95% of the duration of the inspiration phase 16.

As illustrated in FIG. 7, some embodiments of the method 100 may comprise the step of:

controlling 130 the oxygen valve 13 to increase delivered flow of oxygen from the oxygen source 11 to the inspiratory channel 3 during at least a portion of the time period tp, using the control unit 19.

As illustrated in FIG. 7, some embodiments of the method 100 may comprise the step of:

controlling 131 the oxygen valve 13 to increase delivered flow of oxygen from the oxygen source 11 to the inspiratory channel 3 during an initial portion of the time period tp, using the control unit 19.

As illustrated in FIG. 7, some embodiments of the method 100 may comprise the step of:

controlling 132 the oxygen valve 13 to increase delivered flow of oxygen from the oxygen source 11 to the inspiratory channel 3 during an initial portion of the inspiration phase 16, using the control unit 19.

As illustrated in FIG. 7, some embodiments of the method 100 may comprise the step of:

controlling 133 the oxygen valve 13 to deliver a flow of oxygen from the oxygen source 11 to the inspiratory channel 3 from an onset of the inspiration phase 16 to 40%-100% of the duration of the inspiration phase 16, using the control unit 19.

As illustrated in FIG. 7, some embodiments of the method 100 may comprise the step of:

controlling 134 the oxygen valve 13 to increase delivered flow of oxygen from the oxygen source 11 to the inspiratory channel 3 during a final portion of the inspiration phase 16, using the control unit 19.

As illustrated in FIG. 7, some embodiments of the method 100 may comprise the step of:

controlling 135 the oxygen valve 13 to deliver a flow of oxygen from the oxygen source 11 to the inspiratory channel 3 during a second time period tp2 lasting from an onset of the inspiration phase 16 to 10%-30% of the duration of the inspiration phase 16, using the control unit 19.

As illustrated in FIG. 7, some embodiments of the method 100 may comprise the step of:

controlling 136 the oxygen valve 13 to deliver a flow of oxygen from the oxygen source 11 to the inspiratory channel 3 during the expiration phase 17, using the control unit 19.

As illustrated in FIG. 7, some embodiments of the method 100 may comprise the step of:

controlling 137 the blower 7 to deliver a flow of air to the inspiratory channel 3 during the expiration phase 17, using the control unit 19.

According to some embodiments, the breathing apparatus 1 further comprises an input unit 20 connected to the control unit 19, and as illustrated in FIG. 7, the method 100 may comprise the steps of:

employing 140 the input unit 20 to select a mode of operation among at least two different modes of operation, and adapting 141 the time period tp on the basis of the selected mode of operation.

Figure 8:
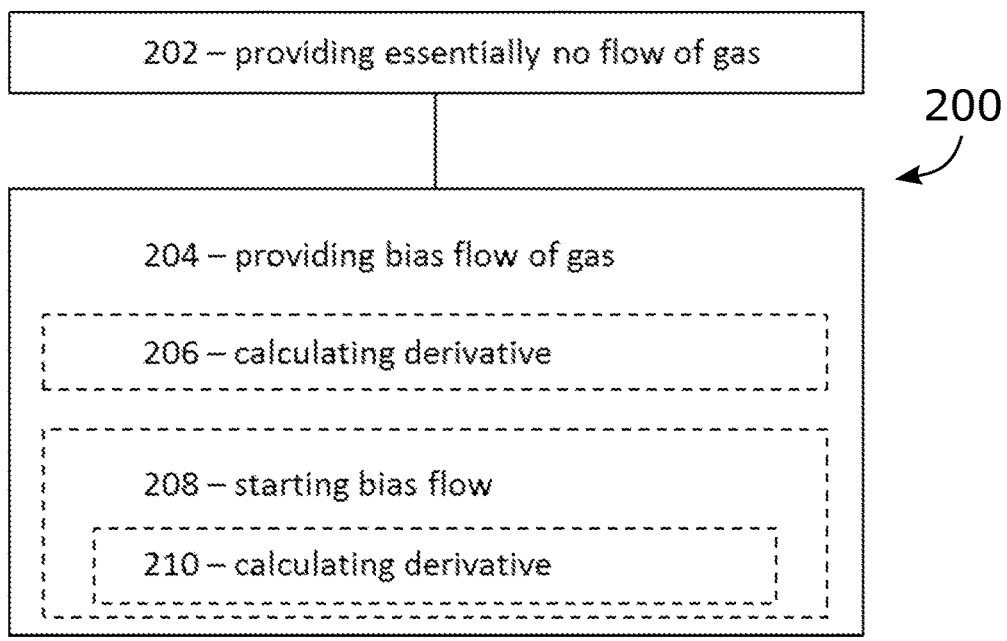
FIG. 8 illustrates a method of controlling a breathing apparatus.

FIG. 8 illustrates a method 200 of controlling a breathing apparatus. The breathing apparatus may be a breathing apparatus 1 as is illustrated in FIG. 1, and some of the features and advantages of the breathing apparatus 1 and the method 200 are explained with reference to FIG. 2-FIG. 6. Therefore, below, reference is made to FIG. 8 as well as to FIG. 1-FIG. 6. The method 200 is a method 200 of controlling a breathing apparatus 1, wherein the breathing apparatus 1 comprises:

an inspiratory channel 3, an expiratory channel 4 and a patient interface 5, wherein the inspiratory channel 3 and the expiratory channel 4 are connected to the patient interface 5, a blower 7 comprising blower driving means 9, wherein the blower 7 is arranged to produce a flow of air to the inspiratory channel 3, an oxygen valve 13 connected to a oxygen source 11, wherein the oxygen valve 13 is configured to selectively deliver a flow of oxygen from the oxygen source 11 to the inspiratory channel 3, a valve 14 configured to prevent flow of gas in a direction from the patient interface 5 in the inspiratory channel 3, a detecting unit 15 configured to detect breathing phases 16, 17, and a control unit 19 connected to the blower driving means 9, the oxygen valve 13 and the detecting unit 15.

The method 200 comprises, during an expiratory phase 17, steps of:

providing 202 substantially no flow of gas in the inspiratory channel 3 during an initial portion of the expiratory phase 17, and providing 204 a bias flow of gas in the inspiratory channel 3 during a final portion of the expiratory phase 17.

Thus, the bias flow of gas required for the breathing apparatus 1 to trigger a new breath is established during the final portion of the expiratory phase 17. Accordingly, the work of breathing during one breath is reduced during the initial portion of the expiratory phase 17.

It has been realised by the inventor(s) that a bias flow is only required during a portion of the expiration phase 17, during which portion a new breath is expected to be triggered. During an initial portion of the expiration phase 17 no bias flow is required. Eliminating the bias flow during the initial portion of the expiration phase 17 reduces the work of breathing of a patient.

According to embodiments of this disclosure, there may be a fixed ratio between the lengths of the initial portion and the final portion of the expiration phase 17. The length of the expiration phase 17 as well as the length of the breath may be set based on the individual needs of a particular patient.

According to embodiments of the method 200, the step of providing 204 the bias flow may be preceded by steps of:

calculating 206 a derivative of an expiratory flow, and starting 208 the bias flow when the derivative of the expiratory flow reaches a threshold level.

In this manner, the breathing apparatus 1 will adapt the start of the bias flow to the actual expiratory flow of a particular patient. Thus, the breathing apparatus 1 will automatically adapt the reduction of work of breathing for the particular patient.

The derivative of the expiratory flow indicates the speed at which the expiratory flow changes. Accordingly, the derivative of the expiratory flow may be utilised for predicting when the expiratory flow will reach a particular flow level, e.g. corresponding to a predetermined bias flow level. Thus, the use of the derivative of the expiratory flow may provide for the commencement of the bias flow being automatically adapted for each patient, and for each breath of a patient.

According to further embodiments of this disclosure, the method may comprise the step of:

starting the bias flow when the expiratory flow reaches a predetermined threshold value. Such a predetermined threshold value may for example be 150% of an intended bias flow.

According to embodiments of this disclosure, the step of starting 208 the bias flow may comprise a step of:

Gradually increasing 210 the bias flow from a zero-flow level to a predetermined bias flow level.

In this manner, the bias flow is gradually ramped up to the predetermined bias flow level, required for the breathing apparatus 1 to trigger a new breath. Thus, irregularities during starting of the bias flow may be avoided, which otherwise accidentally could trigger a new breath.

Suitably, the bias flow is maintained for the remainder of the relevant expiration phase 17 once the provision of the bias flow has commenced, irrespective of whether the expiratory flow should again increase during the relevant expiration phase 17.

Since a breathing apparatus 1 comprising a blower 7 requires a comparatively high bias flow, the method is particularly useful for reducing work of breath in such a breathing apparatus.

Figure 9:
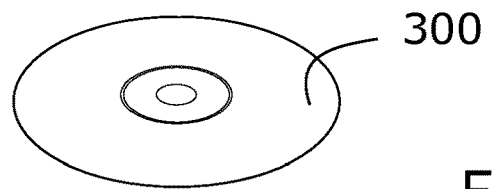
FIG. 9 illustrates a computer program product for performing a method of controlling operation of a breathing apparatus.

FIG. 9 illustrates a computer program product 300 for performing a method of controlling operation of a breathing apparatus 1. The computer program product 300 comprises computer readable code, preferably embedded in the control unit 19, which may be configured to cause the control unit 19, as illustrated in FIG. 1, to perform the method 100 as illustrated in FIG. 7, and/or the method 200 as illustrated in FIG. 8.

Further, the computer program product 300 comprises a computer program for performing a method of controlling operation of a breathing apparatus 1. The computer program comprises computer readable code, preferably embedded in the control unit 19, which may be configured to cause the control unit 19, as illustrated in FIG. 1, to perform the method 100 as illustrated in FIG. 7, and/or the method 200 as illustrated in FIG. 8.

One skilled in the art will appreciate that the method of controlling operation of a breathing apparatus 1 may be implemented by programmed instructions. These programmed instructions are typically constituted by a computer program, which, when it is executed by control unit 19, ensures that the control unit 19 carries out the desired control, such as the method steps described herein. The computer program is usually an embedded part of the computer programme product 300, which comprises a suitable digital storage medium on which the computer program is stored.

The control unit 19 may comprise a calculation unit which may take the form of substantially any suitable type of processor circuit or microcomputer, e.g., a circuit for digital signal processing (digital signal processor, DSP), a Central Processing Unit (CPU), a processing unit, a processing circuit, a processor, an Application Specific Integrated Circuit (ASIC), a microprocessor, or other processing logic that may interpret and execute instructions. The herein utilised expression "calculation unit" may represent a processing circuitry comprising a plurality of processing circuits, such as, e.g., any, some or all of the ones mentioned above. The control unit 19 may further comprise a memory unit, wherein the calculation unit may be connected to the memory unit, which may provide the calculation unit with, for example, stored programme code and/or stored data which the calculation unit may need to enable it to do calculations. The calculation unit may also be adapted to store partial or final results of calculations in the memory unit. The memory unit may comprise a physical device utilised to store data or programs, i.e., sequences of instructions, on a temporary or permanent basis. According to some embodiments, the memory unit may comprise integrated circuits comprising silicon-based transistors. The memory unit may comprise e.g. a memory card, a flash memory, a USB memory, a hard disc, or another similar volatile or non-volatile storage unit for storing data such as e.g. ROM (Read-Only Memory), PROM (Programmable Read-Only Memory), EPROM (Erasable PROM), EEPROM (Electrically Erasable PROM), etc. in different embodiments.

The control unit 19 is connected to components of the breathing apparatus 1 for receiving and/or sending input and output signals. These input and output signals may comprise waveforms, pulses or other attributes which the input signal receiving devices can detect as information and which can be converted to signals processable by the control unit 19. These signals may then be supplied to the calculation unit. Each of the connections to the respective components of the breathing apparatus 1 for receiving and sending input and output signals may take the form of one or more selected from among a cable, a data bus, e.g. a CAN (controller area network) bus, a MOST (media orientated systems transport) bus or some other bus configuration, or a wireless connection.

In the embodiments illustrated, the breathing apparatus 1 comprises a control unit 19 but might alternatively be implemented wholly or partly in two or more control units that operate together or independently.

The computer program product 300 may be provided for instance in the form of a data carrier carrying computer program code for performing at least some of the steps according to some embodiments when being loaded into one or more calculation units of the control unit 19. The data carrier may be, e.g. a CD ROM disc, as is illustrated in FIG. 9, or a ROM (read-only memory), a PROM (programable read-only memory), an EPROM (erasable PROM), a flash memory, an EEPROM (electrically erasable PROM), a hard disc, a memory stick, an optical storage device, a magnetic storage device or any other appropriate medium such as a disk or tape that may hold machine readable data in a non-transitory manner. The computer program product may furthermore be provided as computer program code on a server and may be downloaded to the control unit 19 remotely, e.g., over an Internet or an intranet connection, or via other wired or wireless communication systems.

It is to be understood that the foregoing is illustrative of various example embodiments and that the invention is defined only by the appended claims. A person skilled in the art will realize that the example embodiments may be modified, and that different features of the example embodiments may be combined to create embodiments other than those described herein, without departing from the scope of the this disclosure, as defined by the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A breathing apparatus, comprising:
an inspiratory channel, an expiratory channel and a patient interface, wherein the inspiratory channel and the expiratory channel are connected to the patient interface;
a blower including a blower driving arrangement, wherein the blower is arranged to produce a flow of air to the inspiratory channel;
an oxygen valve arranged to be connected to an oxygen source, wherein the oxygen valve is configured to selectively deliver a flow of oxygen from the oxygen source to the inspiratory channel;
a valve configured to prevent flow of gas in a direction from the patient interface in the inspiratory channel;
a detecting unit configured to detect breathing phases; and
a control unit connected to the blower driving arrangement, the oxygen valve and the detecting unit,
wherein the control unit is configured to control the blower driving arrangement so that the blower produces substantially no flow of air to the inspiratory channel during a time period tp starting during an inspiration phase, after 30% duration thereof, and ending the latest upon initiation of the subsequent inspiration phase,
and wherein the control unit is configured to control the oxygen valve to increase the flow of oxygen delivered from the oxygen source to the inspiratory channel during at least a portion of the time period tp.

2. The breathing apparatus according to claim 1, wherein the control unit is configured to deactivate the blower driving arrangement during the time period tp.

3. The breathing apparatus according to claim 1, wherein the time period tp starts during the inspiration phase and ends during the subsequent expiration phase.

4. The breathing apparatus according to claim 3, wherein the time period tp starts during a final portion of the inspiration phase and ends during an onset of the subsequent expiration phase.

5. The breathing apparatus according to claim 4, wherein the final portion of the inspiration phase is between 65% and 95% of the duration of the inspiration phase.

6. The breathing apparatus according to claim 3, wherein the time period tp starts during a final portion of the inspiration phase and ends during 50%-75% of a duration of the subsequent expiration phase.

7. The breathing apparatus according to claim 1, wherein the control unit is configured to control the oxygen valve to increase delivered flow of oxygen from the oxygen source to the inspiratory channel during an initial portion of the time period tp.

8. The breathing apparatus according to claim 1, wherein the control unit is configured to control the oxygen valve to increase delivered flow of oxygen from the oxygen source to the inspiratory channel during an initial portion of the inspiration phase.

9. The breathing apparatus according to claim 1, wherein the control unit is configured to control the oxygen valve to deliver a flow of oxygen from the oxygen source to the inspiratory channel from an onset of the inspiration phase to 40%-100% of the duration of the inspiration phase.

10. The breathing apparatus according to claim 1, wherein the control unit is configured to control the oxygen valve to increase delivered flow of oxygen from the oxygen source to the inspiratory channel during a final portion of the inspiration phase.

11. The breathing apparatus according to claim 1, wherein the control unit is configured to control the oxygen valve to deliver a flow of oxygen from the oxygen source to the inspiratory channel during a second time period tp2 lasting from an onset of the inspiration phase to 10%-30% of the duration of the inspiration phase.

12. The breathing apparatus according to claim 1, wherein the control unit is configured to control the oxygen valve to deliver a flow of oxygen from the oxygen source to the inspiratory channel during the expiration phase.

13. The breathing apparatus according to claim 1, wherein the control unit is configured to control the blower to deliver a flow of air to the inspiratory channel during the expiration phase.

14. The breathing apparatus according to claim 1, further comprising:
an input unit connected to the control unit, wherein the input unit is configured to provide selection of a mode of operation among at least two different modes of operation, and wherein the control unit is configured to adapt the time period tp on the basis of the selected mode of operation.

15. The breathing apparatus according to claim 14, wherein the control unit is configured to control the oxygen valve on the basis of the selected mode of operation, and wherein the at least two different modes of operation comprises at least two modes of operation in which different operational aspects of the breathing apparatus are optimized.

16. The breathing apparatus according to claim 1, further comprising:
at least one battery connected to the blower driving arrangement and configured to supply driving energy to the blower driving arrangement.

17. A method for controlling a breathing apparatus, wherein the breathing apparatus comprises:
an inspiratory channel, an expiratory channel and a patient interface, wherein the inspiratory channel and the expiratory channel are connected to the patient interface;
a blower comprising a blower driving arrangement, wherein the blower is arranged to produce a flow of air to the inspiratory channel;
an oxygen valve connected to an oxygen source, wherein the oxygen valve is configured to selectively deliver a flow of oxygen from the oxygen source to the inspiratory channel;
a valve configured to prevent flow of gas in a direction from the patient interface in the inspiratory channel;
a detecting unit configured to detect breathing phases; and
a control unit connected to the blower driving arrangement, the oxygen valve and the detecting unit,
wherein the method comprises the steps of:
detecting breathing phases, using the detecting unit; and
controlling the blower driving arrangement, using the control unit, so that the blower produces substantially no flow of air to the inspiratory channel during a time period tp starting during an inspiration phase, after 30% duration thereof, and ending the latest upon initiation of the subsequent inspiration phase,
and wherein the control unit is configured to control the oxygen valve to increase the flow of oxygen delivered from the oxygen source to the inspiratory channel during at least a portion of the time period tp.

18. The method according to claim 17, further comprising the step of:
deactivating the blower driving arrangement during the time period tp, using the control unit.

19. The method according to claim 17, further comprising the steps of:
starting the time period tp during the inspiration phase; and
ending the time period tp during the subsequent expiration phase.

20. The method according to claim 17, further comprising the steps of:
starting the time period tp during a final portion of the inspiration phase; and
ending the time period tp during an onset of the subsequent expiration phase.

21. The method according to claim 20, wherein the final portion of the inspiration phase is between 65% and 95% of the duration of the inspiration phase.

22. The method according to claim 17, further comprising the steps of:
starting the time period tp during a final portion of the inspiration phase; and
ending the time period tp during 50%-75% of a duration of the subsequent expiration phase.

23. The method according to claim 17, further comprising the step of: controlling the oxygen valve to increase delivered flow of oxygen from the oxygen source to the inspiratory channel during an initial portion of the time period tp, using the control unit.

24. The method according to claim 17, further comprising the step of: controlling the oxygen valve to increase delivered flow of oxygen from the oxygen source to the inspiratory channel during an initial portion of the inspiration phase, using the control unit.

25. The method according to claim 17, further comprising the step of: controlling the oxygen valve to deliver a flow of oxygen from the oxygen source to the inspiratory channel from an onset of the inspiration phase to 40%-100% of the duration of the inspiration phase, using the control unit.

26. The method according to claim 17, further comprising the step of: controlling the oxygen valve to increase delivered flow of oxygen from the oxygen source to the inspiratory channel during a final portion of the inspiration phase, using the control unit.

27. The method according to claim 17, further comprising the step of: controlling the oxygen valve to deliver a flow of oxygen from the oxygen source to the inspiratory channel during a second time period tp2 lasting from an onset of the inspiration phase to 10%-30% of the duration of the inspiration phase, using the control unit.

28. The method according to claim 17, further comprising the step of: controlling the oxygen valve to deliver a flow of oxygen from the oxygen source to the inspiratory channel during the expiration phase, using the control unit.

29. The method according to claim 17, further comprising the step of: controlling the blower to deliver a flow of air to the inspiratory channel during the expiration phase, using the control unit.

30. The method according to claim 17, wherein the breathing apparatus further comprises an input unit connected to the control unit and wherein the method further comprises the steps of:
employing the input unit to select a mode of operation among at least two different modes of operation; and
adapting the time period tp on the basis of the selected mode of operation.

31. A computer program for performing a method for controlling operation of a breathing apparatus, wherein the computer program comprises computer readable code embedded in a control unit of the breathing apparatus and configured to cause the control unit to operate the breathing apparatus so as to perform the method according to claim 17.

* * * * *